United States Patent
Hu

(10) Patent No.: US 9,428,450 B2
(45) Date of Patent: *Aug. 30, 2016

(54) PROCESS FOR PRODUCING TAURINE FROM ALKALI TAURINATES

(71) Applicant: Songzhou Hu, Princeton, NJ (US)

(72) Inventor: Songzhou Hu, Princeton, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/120,046

(22) Filed: Apr. 18, 2014

(65) Prior Publication Data

US 2015/0299113 A1  Oct. 22, 2015

(51) Int. Cl.
  *C07C 303/32* (2006.01)
  *C07C 303/02* (2006.01)
  *C07C 303/44* (2006.01)

(52) U.S. Cl.
  CPC .......... *C07C 303/32* (2013.01); *C07C 303/02* (2013.01); *C07C 303/44* (2013.01)

(58) Field of Classification Search
  None
  See application file for complete search history.

(56) References Cited

U.S. PATENT DOCUMENTS

| | | | | |
|---|---|---|---|---|
| 1,932,907 A | * | 10/1933 | Nicodemus | C07C 309/14 562/102 |
| 1,999,614 A | * | 4/1935 | Ossenbeck | C07C 309/14 562/104 |
| 2,820,818 A | | 1/1958 | Sexton | |

FOREIGN PATENT DOCUMENTS

| | | | |
|---|---|---|---|
| CN | 101486669 | * | 7/2009 |
| CN | 101508657 | * | 8/2009 |
| CN | 101508658 | * | 8/2009 |
| CN | 101508659 | * | 8/2009 |
| DE | 219 023 | | 2/1985 |
| WO | WO 01/77071 | | 10/2001 |

OTHER PUBLICATIONS

Database Caplus Chemical Abstracts Service, Columbus, Ohio, US; Database Accession No. 1993:233480, Abstract of JP 04352760, Dec. 7, 1992, Nippon Catalytic Chem Ind, Japan.*
Database Caplus Chemical Abstracts Service, Columbus, Ohio, US; Database Accession No. 1986:34336, Abstract of DD 219023 Bach et al., Feb. 20, 1985.*

* cited by examiner

*Primary Examiner* — Karl J Puttlitz

(74) *Attorney, Agent, or Firm* — Graham Curtin, P.A.

(57) ABSTRACT

A process for producing taurine from alkali ditaurinate or alkali tritaurinate, or their mixture, comprising the conversion of alkali ditaurinate to dialkali ditaurinate or alkali tritaurinate to trialkali tritaurinate, or their mixture, the ammonolysis reaction of ammonia added to a solution of dialkali ditaurinate or trialkali tritaurinate, or their mixture, to yield alkali taurinate, removing excess ammonia from the foregoing and neutralizing alkali taurinates with an acid to form a crystalline suspension of taurine, and recovering taurine by means of solid-liquid separation.

7 Claims, 2 Drawing Sheets

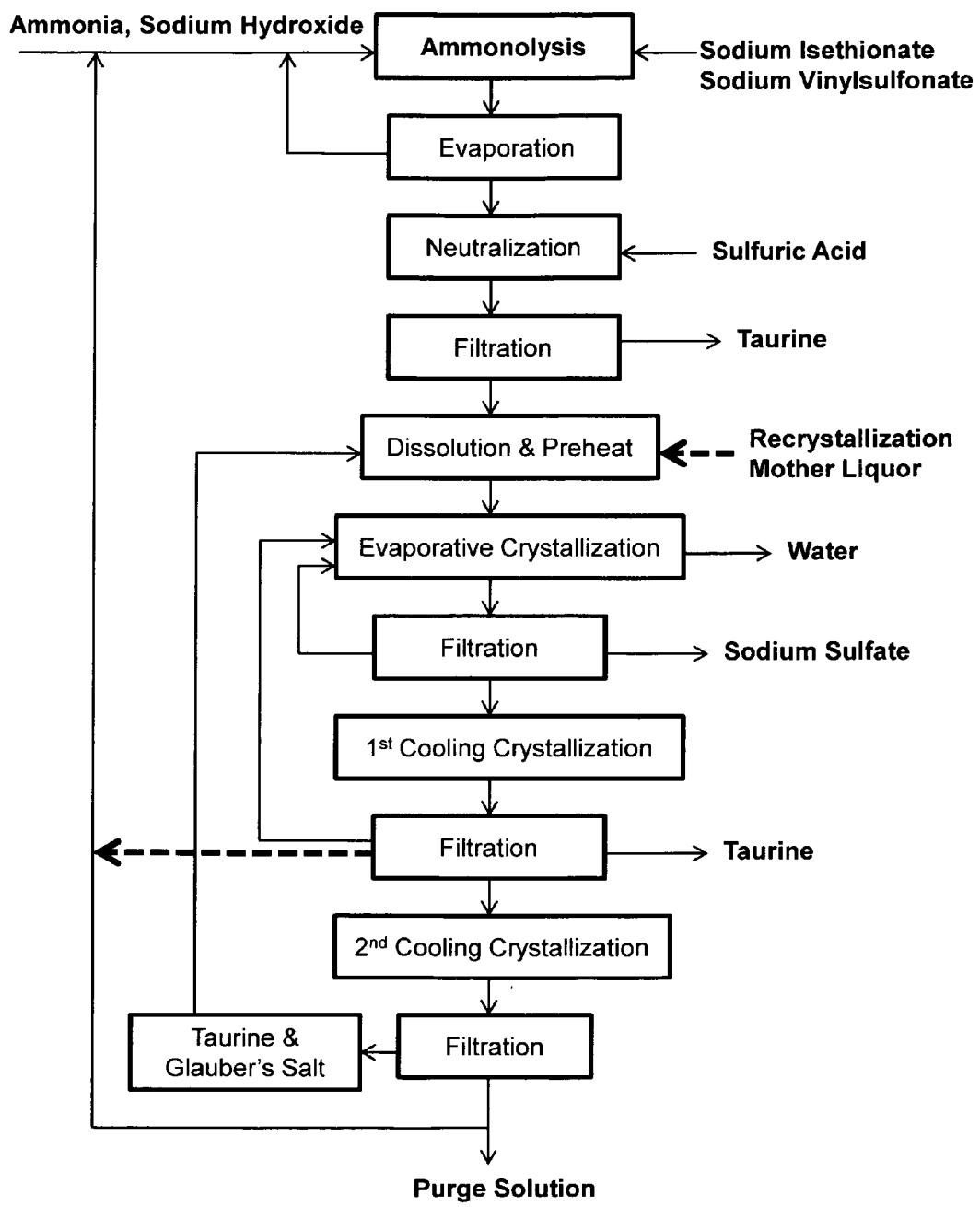
Fig. 1 Schematic Flowchart for the Cyclic Production of Taurine

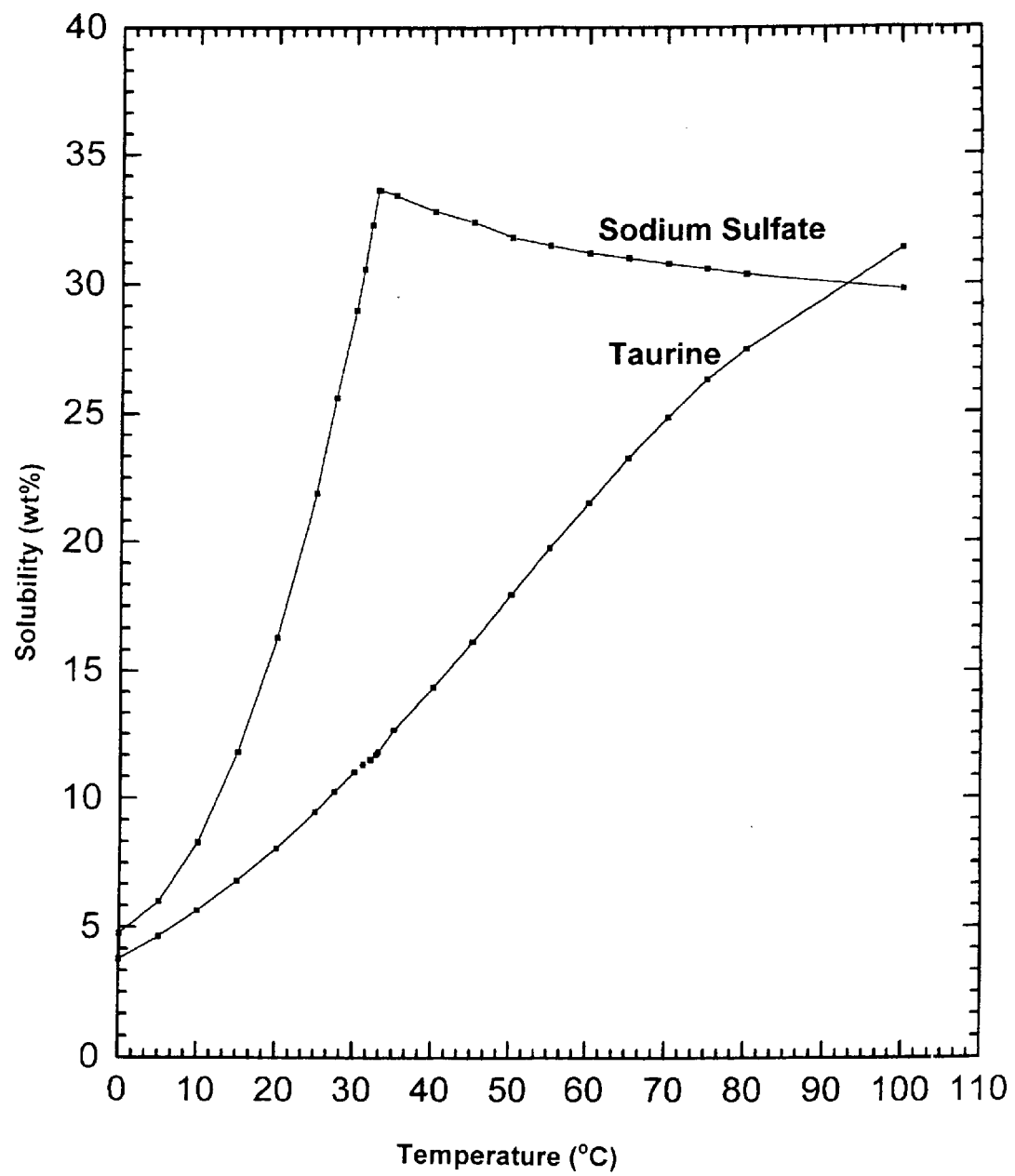
Fig. 2 Solubility Curve of Taurine and Sodium Sulfate in Water

PROCESS FOR PRODUCING TAURINE FROM ALKALI TAURINATES

TECHNICAL FIELD

The present invention relates to a cyclic process for the production of taurine from alkali isethionate and from alkali vinyl sulfonate in a high overall yield, i.e., greater than 90%, in particular, greater than 95%, by continuously converting the byproducts of the ammonolysis reaction, alkali ditaurinate and alkali tritaurinate, to alkali taurinate.

BACKGROUND OF THE INVENTION

Taurine can be referred to as 2-aminoethanesulfonic acid and is one of the amino sulfonic acids found in the tissues of many animals. Taurine is an extremely useful compound because it has such pharmacological effects as detoxification effect, fatigue-relieving effect and nourishing and tonifying effect. As a result, taurine finds wide applications as an essential ingredient for human and animal nutrition.

Taurine is currently produced in an amount of over 50,000 tons per year from ethylene oxide and monoethanolamine. At present time, most of the taurine is produced from ethylene oxide, following a three-step process: (1) the addition reaction of ethylene oxide with sodium bisulfite to yield sodium isethionate; (2) the ammonolysis of sodium isethionate to yield sodium taurinate; (3) the neutralization with an acid, i.e, hydrochloric acid and, preferably, sulfuric acid, to generate taurine and inorganic salts.

Although the ethylene oxide process is well established and widely practiced in commercial production, the overall yield is not very high, less than 80%. Moreover, the process generates a large amount of waste stream that is increasingly difficult to dispose of.

The first stage of the ethylene oxide process, the addition reaction of ethylene oxide with sodium bisulfate, is known to yield sodium isethionate in high yield, practically quantitative, as disclosed in U.S. Pat. No. 2,820,818 under specified conditions.

Therefore, the problems encountered in the production of taurine from the ethylene oxide process arise from the ammonolysis of sodium isethionate and from the separation of taurine from sodium sulfate.

According to the copending applications U.S. Ser. No. 13/999,203 and U.S. Ser. No. 13/999,439, these same issues are also encountered in the production of taurine from ethanol and ethylene, respectively. Sodium isethionate is a key common intermediate and the ammonolysis of sodium isethionate is an important step in the ethanol and ethylene processes.

U.S. Pat. No. 1,932,907 discloses that sodium taurinate is obtained in a yield of 80%, when sodium isethionate undergoes ammonolysis reaction in a molar ratio of 1:6.8 for 2 hrs at 240 to 250° C. U.S. Pat. No. 1,999,614 describes the use of catalysts, i.e., sodium sulfate, sodium sulfite, and sodium carbonate, in the ammonolysis reaction. A mixture of sodium taurinate and sodium ditaurinate is obtained in a yield as high as 97%. However, the percentage for sodium taurinate and sodium ditaurinate in the mixture is not specified.

DD 219 023 describes detailed results on the product distribution of the ammonolysis reaction of sodium isethionate. When sodium isethionate undergoes the ammonolysis reaction with 25% aqueous ammonia in a molar ratio of 1:9 at about 280° C. for 45 minutes in the presence of sodium sulfate and sodium hydroxide as catalyst, the reaction products comprise 71% of sodium taurinate and 29% of sodium di- and tri-taurinate.

WO 01/77071 is directed to a process for the preparation of ditaurine by heating an aqueous solution of sodium taurinate at a temperature of 210° C. in the presence of a reaction medium. A mixture of sodium taurinate and sodium ditaurinate is obtained.

From these prior arts, it is therefore concluded that the ammonolysis of sodium isethionate invariably yields a mixture of sodium taurinate, sodium ditaurinate, and sodium tritaurinate. The percentage yield of sodium taurinate has not been more than 80%.

In order to obtain taurine from sodium taurinate, U.S. Pat. No. 2,693,488 discloses a method of using ion exchange resins, first strongly acid ion exchange resin in hydrogen form, then an anion exchange resin in basic form. This process is complicated and requires the use of large quantity of acid and base to regenerate the ion exchange resins in each production cycle.

On the other hand, CN101508657, CN101508658, CN101508659, and CN101486669 describe a method of using sulfuric acid to neutralize sodium taurinate to obtain a solution of taurine and sodium sulfate. Crude taurine is easily obtained by filtration from a crystalline suspension of taurine after cooling. However, the waste mother liquor still contains taurine, sodium sulfate, and other unspecified organic impurities. It is desirable to have available a process for further separation of these components to achieve an economical process and to reduce the disposal of waste stream.

It is, therefore, an object of the present invention to disclose a cyclic process for the production of taurine from alkali isethionate and from alkali vinyl sulfonate in a high overall yield, i.e., greater than 90%, in particular, greater than 95%. According to the process in the present invention, sodium ditaurinate and sodium tritaurinate, byproducts from the ammonolysis of sodium isethionate or sodium vinyl sulfonate, are continuously converted to sodium taurinate in the ammonolysis stage.

It is another object of the present invention to disclose a process for the preparation of pure sodium ditaurinate and pure sodium tritaurinate, and their conversion to sodium taurinate. When sodium ditaurinate and sodium tritaurinate are reacted with aqueous ammonia under ammonolysis reaction conditions, a mixture of similar compositions of sodium taurinate, ditaurinate, and tritaurinate is formed in an equilibrium state. This novel finding renders the cyclic process possible.

It is a further object of the present invention to disclose a process for the complete separation of taurine and sodium sulfate from each other and from the byproducts, i.e., sodium ditaurinate and sodium tritaurinate. According to the process in the present invention, the residual taurine and sodium sulfate are separated from sodium ditaurinate and sodium tritaurinate by a process of co-crystallization of taurine and Glauber's salt at a temperature from 0 to 20° C. The crystalline mixture of taurine and sodium sulfate is then separated from each other, while the mother liquor, consisting of taurine, monosodium ditaurinate, and monosodium tritauriante, is suitable for recycling to the ammonolysis step to prepare sodium taurinate.

DESCRIPTION OF THE DRAWINGS

FIG. 1. Schematic flowchart for the cyclic production of taurine from sodium isethionate and sodium vinyl sulfate.

FIG. 2. Solubility curves for taurine and sodium sulfate in water.

DESCRIPTION OF THE INVENTION

The present invention relates to a cyclic process for the production of taurine from alkali isethionate, which is a key intermediate for the ethylene oxide, ethanol, and ethylene processes. This cyclic process is also applied to the production of taurine from alkali vinyl sulfonate, another intermediate for the ethanol and ethylene processes.

For the production of taurine, sodium isethionate and sodium vinyl sulfonate are preferably used, but other alkali metals, i.e., lithium, potassium, and cesium, are equally suitable. In the drawings and following description, only sodium is used in replace of alkali metals to describe the process.

In order to achieve the cyclic process, the present invention discloses a novel finding and process for converting sodium ditaurinate and sodium tritaurinate, byproducts of the ammonolysis of sodium isethionate, to sodium taurinate under the ammonolysis conditions. According to the cyclic process in the present invention, sodium isethionate and sodium vinyl sulfonate are converted to sodium taurinate in a practically quantitative yield. A complete separation of taurine with sodium sulfate according to the process in the present invention ensures that taurine is obtained in high yield, i.e., greater than 90%, in particular greater than 95% on the basis of sodium isethionate or sodium vinyl sulfonate.

Although sodium ditaurinate and sodium tritaurinate are mentioned in the prior arts, preparation of pure products is not known. The present invention describes a method for the preparation of pure sodium ditaurinate and pure sodium tritaurinate from diethanolamine and triethanolamine, respectively.

To prepare sodium ditaurinate, diethanolamine is first reacted with excess thionyl chloride to form bis(2-chloroethyl)amine hydrochloride in quantitative yield, which undergoes sulfonation with sodium sulfite to yield the expected product. When triethanolamine is used in the same sequence of reactions, tris(2-chloroethyl)amine hydrochloride is obtained as an intermediate, and disodium tritaurinate is obtained as an aqueous solution, along with sodium chloride. The reaction schemes are as follows:

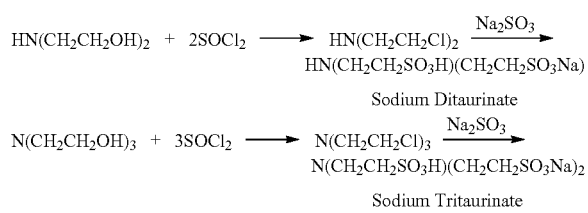

When sodium ditaurinate and sodium tritaurinate are subjected to the ammonolysis reaction in aqueous ammonia under the same conditions at a temperature of 220° C. for 2 hours, a mixture of similar compositions, i.e., sodium taurinate (74%), sodium ditaurinate (23%), and sodium tritaurinate (3%), is obtained. Clearly, an equilibrium state is reached among the three taurinates, irrespective of the starting materials.

This novel finding renders possible the cyclic process for preparing taurine from sodium isethionate and from sodium vinyl sulfonate, because the inevitable byproducts of the ammonolysis step, i.e., sodium ditaurinate and sodium tritaurinate, can be continuously converted to sodium taurinate in each successive cycle.

FIG. 1 describes the detailed unit operations for the cyclic process for the production and isolation of taurine from sodium isethionate. The cycle is equally applicable for the production of taurine from sodium vinyl sulfonate.

The cyclic process starts from the ammonolysis of sodium isethionate or sodium vinyl sulfonate in aqueous ammonia at a temperature of 150 to 270° C. under a pressure from the autogenous to 260 bars, and optionally, in the presence of catalysts. Usually, catalysts are the alkaline salts of sodium, potassium and lithium. Such salts are sodium hydroxide, potassium hydroxide, lithium hydroxide, sodium carbonate, potassium carbonate, lithium carbonate, sodium sulfate, sodium sulfite, potassium sulfate, potassium sulfite. Any one or a combination of two or more these salts can be used as catalyst to influence the reaction.

After the ammonolysis reaction, the excess ammonia are dispelled from the reaction solution and reclaimed for reuse. Sodium taurinate is obtained, along with sodium ditaurinate, sodium tritaurinate, and unreacted sodium isethionate.

The strongly basic solution is neutralized with sulfuric acid to pH 5-7 to yield mainly taurine, sodium sulfate, sodium ditaurinate, and sodium tritaurinate. The content of taurine and sodium sulfate is in a molar ratio of 1:0.5 to 1:0.6, and nearly the same in terms of their weight.

The initial solution is optionally concentrated, then cooled to 28 to 35° C., to crystallize taurine. The first batch of crude taurine is obtained by filtration, while sodium sulfate remains in solution. Lower temperature is to be avoided to prevent the crystallization of sodium sulfate.

It is important to point out that sodium sulfate has the maximum solubility at a temperature of 33° C. as shown in FIG. 2. The solubility of sodium sulfate decreases slightly from 33 to 100° C., but drastically from 33 to 0° C. Moreover, sodium sulfate crystallizes as anhydrous form above 40° C., but as Glauber's salt, i.e., sodium sulfate decahydrate at a temperature below 30° C.

The mother liquor is now consisted of about 30% of sodium sulfate and about 10% of taurine, along with various percentages of sodium ditaurinate and sodium tritaurinate. This solution is concentrated to about one half to one third of its original volume in an evaporative crystallizer, at a temperature from 70 to 95° C., preferably 75 to 85° C., to yield a suspension of sodium sulfate, which is removed by filtration at the same temperature. The temperature is kept high enough to prevent the crystallization of taurine at this stage.

The filtration mother liquor, now saturated with sodium sulfate and rich in taurine, is cooled to 33-35° C. in the $1^{st}$ cooling crystallizer to crystallize the second crop of crude taurine.

The cycle of evaporative crystallization at higher temperature, preferably from 75 to 85° C., to remove sodium sulfate, and the first cooling crystallization at lower temperature, preferably at 33-35° C., can be continued until the solid content of impurities, mainly sodium ditaurinate and sodium tritaurinate, accumulates to about 30% of the solid content in the mother liquor.

The mother liquor from the first cooling crystallization stage can be returned to the ammonolysis step. Preferably, the mother liquor is cooled to 10 to 15° C. in the $2^{nd}$ cooling crystallizer to co-crystallize taurine and sodium sulfate decahydrate, i.e., Glauber's salt. The co-crystalline mixture is removed from the mother liquor by centrifuge and returned to a dissolution and preheat unit for the evaporative crystallization step. It becomes apparent from FIG. 2 that lower temperature may be used, but excessive cooling is required to be economical. At higher temperature, removal of sodium sulfate is not complete.

The mother liquor from the second cooling crystallization stage is usually comprised of 25-30% of sodium ditaurinate and tritaurinate, 5-7% of taurine, and 7-8% of sodium sulfate. Sodium hydroxide is then added in an amount sufficient to turn taurine to sodium taurinate, sodium ditaurinate to disodium ditaurinate, and disodium tritaurinate to trisodium tritaurinate. In other words, the molar amount of sodium hydroxide is equal to, or slightly more than, the molar amount of total taurinates in the solution. This solution is then saturated with ammonia to 15 to 28% and returned to the ammonolysis step. Optionally, this solution may be combined with a new batch of sodium isethionate or sodium vinyl sulfonate for the ammonolysis step.

Some of the mother liquor from the $2^{nd}$ cooling crystallization needs to be purged from the cycle, when uncharacterized impurities start to adversely influence the quality of the product. The amount of purge solution in each cycle depends on the quality of starting materials, in particular, sodium isethionate and sodium vinyl sulfonate. If crude sodium isethionate in the ethylene oxide process is used, purge is required in about every five to eight cycles, because ethylene glycol, a byproduct from the reaction of ethylene oxide with water, starts to accumulate. If sodium isethionate is prepared from ethanol and ethylene, no purge is necessary at all.

Crude taurine obtained in the cyclic process is recrystallized from deionized water one or more times to yield a product of pharmaceutical grade. The recrystallization mother liquor may be reused several times until it affects the quality of the product obtained. This mother liquor, consisting of residual taurine, sodium sulfate, and impurities, is then sent to dissolution and preheat unit for the evaporative crystallization.

It should be appreciated that no waste is generated in the cyclic process according to the present invention for the production of taurine from ethanol and ethylene, because sodium sulfate, discharged in the cyclic process, is recycled continuously to prepare sodium isethionate and sodium vinyl sulfonate.

The process according to the present invention can be carried out discontinuously, semi-continuously, and continuously.

EXAMPLES

The following examples will illustrate the practice of this invention but are not intended to limit its scope.

Example 1

This example relates to the preparation of sodium ditaurinate and its reaction with aqueous ammonia under ammonolysis reaction conditions.

Into a 1 L flask, equipped a refluxing condenser, is added 31.5 g (0.30 mole) of diethanolamine and 300 mL of dichloroethane, then 51.0 mL of thionyl chloride. Solid suspension formed immediately after the addition of thionyl chloride and then dissolved upon warming to 50° C. During refluxing, the solid suspension is dissolved and then the crystalline solid appears. The crystalline suspension is refluxed while being stirred for 3 hrs. The reaction is quenched by adding 20 mL of methanol and the solvents are removed under vacuum. A white crystalline material, bis(2-chloroethyl)amine hydrochloride, weighted 53.0 g, is obtained in a quantitative yield.

To the flask is added 500 mL of deionized water, 100 g of sodium sulfite. The solution is stirred at a temperature first at 50-60° C. for 3 hrs, then at 95° C. for 4 hrs. HPLC and LC-MS shows complete conversion of the starting material to the desired sodium ditaurinate.

The excess sodium sulfite is destroyed by addition of 40 mL of 30% hydrochloric acid, followed by careful adjustment of pH to 6-7 with sodium carbonate. The solution consists of practically pure sodium ditaurinate and sodium chloride. The solution may be used directly in the ammonolysis reaction.

To obtain pure sodium ditaurinate, the aqueous solution is vacuum dried to give a white solid. Into the flask is added 600 mL of anhydrous methanol, and the suspension is refluxed for 30 minutes to dissolve sodium ditaurinate in methanol. After filtration to remove sodium chloride, the methanol solution is cooled to room temperature to crystallize pure sodium ditaurinate, which is used as analytical standard.

Crude sodium ditaurinate, prepared from 0.30 mole of diethanolamine, is dissolved in 300 mL of water containing 26.0 g of sodium hydroxide. The solution is then mixed with 600 mL of 25% aqueous ammonia and heated in an autoclave at 220° C. for 2 hrs.

HPLC analysis of the reaction solution shows the formation of sodium taurinate (74%), sodium ditaurinate (24%), and sodium tritaurinate (2%) on the molar basis.

Example 2

This example relates to the preparation of sodium tritaurinate and its reaction with aqueous ammonia under ammonolysis reaction conditions.

Into a 1 L flask, equipped with a refluxing condenser, is added 29.8 g (0.20 mole) of triethanolamine, 300 mL of dichloroethane, then 51.0 mL of thionyl chloride. The mixture is heated to reflux for 4 hrs. The reaction is quenched by adding 20 mL of methanol. Removal of solvent gives a white crystalline mass of tris(2-chloroethylamine) hydrochloride in quantitative yield.

To the flask is added 500 mL of deionized water, 100 g of sodium sulfite. An oil phase is separated first. After heating at 60° C. for 2 hrs and 98° C. for 5 hrs, the oil phase disappears and a clear solution is obtained. HPLC and LC-MS shows complete conversion of the starting material to the desired sodium tritaurinate.

The crude reaction solution is transferred to a 2 L autoclave, to which 26 g of sodium hydroxide and 600 mL of 25% aqueous ammonia are added. The autoclave is heated to 220° C. for 2 hrs to carry out the ammonolysis reaction.

HPLC and LC-MS analysis shows that sodium tritaurinate is converted to a mixture of sodium taurinate (72%), sodium ditaurinate (23%), and sodium tritaurinate (5%) on the molar basis.

Example 3

This example demonstrates the conversion of sodium ditaurinate and sodium tritaurinate in the recrystallization mother liquor to sodium taurinate.

To 200 mL of the mother liquor from $2^{nd}$ cooling crystallization stage, composed of sodium ditaurinate (25% by wt), sodium tritaurinate (3% by wt), taurine (5% by wt), and sodium sulfate (6% by wt), is added 15 g of sodium hydroxide, 500 mL of 25% aqueous ammonia. The solution is heated in a 2 L autoclave at 220° C. for 2 hrs to carry out the ammonolysis reaction.

HPLC and LC-MS analysis shows that the reaction solution is comprised of the following taurinates: sodium taurinate (76%), sodium ditaurinate (21%), and sodium tritaurinate (3%) on the molar basis.

Example 4

This example is directed to a process for the separation of taurine from sodium sulfate and from sodium ditaurinate and sodium tritaurinate.

A starting solution is prepared by first boiling the solution from the ammonolysis reaction to remove excess ammonia, and then adding enough sulfuric acid to pH 5-7. The solution is consisted of 30% taurine, 26% sodium sulfate, and 7% sodium di- and tri-taurinates.

2000 g of the starting solution is cooled from 80° C. to 33° C. to form a slurry consisting essentially of the first crop of crystallized taurine, which is separated by filtration at 33° C. and washed with 100 g of cold water. The recovered taurine is dried and weighed 398 g.

The separated mother liquor, weighed 1580 g, is boiled to evaporate to 900 g to form a slurry of sodium sulfate. This slurry is cooled to 80° C. and filtered to recover sodium sulfate, weighed 304 g.

The mother liquor, containing 202 g of taurine and 216 g of sodium sulfate, is cooled to 33° C. to form a second slurry of taurine. After filtration and washing with cold water, 124 g of taurine is obtained.

The mother liquor from the previous step, now containing 78 of taurine and 216 g of sodium sulfate, is cooled to 10° C. in 2 hrs to obtain slurry of taurine and Glauber's salt. The crystalline solid is obtained as a mixture of taurine and sodium sulfate decahydrate.

This final mother liquor, about 500 g, is consisted of sodium ditaurinate and tritaurinate (28%, 140 g), taurine (24 g, 4.8%), and sodium sulfate (35 g, 7%). This solution is used for the ammonolysis reaction.

It will be understood that the foregoing examples, explanation, drawings are for illustrative purposes only and that in view of the instant disclosure various modifications of the present invention will be self-evident to those skilled in the art and are to be included within the spirit and purview of this application and the scope of the appended claims.

What is claimed is:

1. A process for the production of taurine from alkali ditaurinate or alkali tritaurinate, or their mixture, comprising,
    (a) adding an alkali hydroxide to a solution of alkali ditaurinate, or alkali tritaurinate or their mixture, to prepare a solution of dialkali ditaurinate, or trialkali tritauriante or their mixture,
    (b) adding an excess amount of ammonia to a solution of dialkali ditaurinate, or dialkali tritaurinate, or their mixture, and subjecting the solution to ammonolysis reaction to yield a mixture of alkali taurinates,
    (c) removing excess ammonia from (b) and neutralizing alkali taurinates with an acid to form a crystalline suspension of taurine, and
    (d) recovering taurine by means of solid-liquid separation.

2. The process according to claim 1, wherein alkali ditaurinate and alkali tritaurinate are prepared from diethanolamine and triethanolamine, respectively.

3. The process according to claim 1, wherein alkali ditaurinate, alkali tritaurinate, and their mixture are the byproducts in the production of taurine by the ammonolysis reaction of alkali isethionate or alkali vinyl sulfonate.

4. The process according to claim 1, wherein the catalysts for the ammonolysis reaction are sodium hydroxide, potassium hydroxide, lithium hydroxide, sodium carbonate, potassium carbonate, lithium carbonate, sodium sulfate, sodium sulfite, potassium sulfate, and potassium sulfite.

5. The process according to claim 1, wherein alkali metals are lithium, sodium, and potassium.

6. The process according to claim 1, wherein the acids are sulfuric acid, hydrochloric acid, nitric acid, hydrobromic acid, sulfurous acid, sulfur dioxide, and carbon dioxide.

7. The process according to claim 1, wherein the ammonolysis reaction is carried out at a temperature from 150 to 280° C. and under a pressure from autogenous to 260 bar.

* * * * *

(12) INTER PARTES REVIEW CERTIFICATE (2265th)

United States Patent
Hu

(10) Number: US 9,428,450 K1
(45) Certificate Issued: Aug. 17, 2021

(54) PROCESS FOR PRODUCING TAURINE FROM ALKALI TAURINATES

(71) Applicant: Songzhou Hu

(72) Inventor: Songzhou Hu

(73) Assignee: VITAWORKS IP, LLC

Trial Number:

IPR2018-01766 filed Sep. 28, 2018

Inter Partes Review Certificate for:

Patent No.: 9,428,450
Issued: Aug. 30, 2016
Appl. No.: 14/120,046
Filed: Apr. 18, 2014

The results of IPR2018-01766 are reflected in this inter partes review certificate under 35 U.S.C. 318(b).

INTER PARTES REVIEW CERTIFICATE
U.S. Patent 9,428,450 K1
Trial No. IPR2018-01766
Certificate Issued Aug. 17, 2021

AS A RESULT OF THE INTER PARTES REVIEW PROCEEDING, IT HAS BEEN DETERMINED THAT:

Claims 1 and 3-7 are cancelled.

\* \* \* \* \*